United States Patent
Yoo et al.

(10) Patent No.: US 10,697,971 B2
(45) Date of Patent: Jun. 30, 2020

(54) DIAGNOSTIC METHOD OF LIVER CANCER USING α-FETOPROTEIN DERIVED GLYCOPEPTIDES BY MASS SPECTROMETRY

(71) Applicant: KOREA BASIC SCIENCE INSTITUTE, Daejeon (KR)

(72) Inventors: Jong Shin Yoo, Seoul (KR); Kwang Hoe Kim, Chungcheongbuk-do (KR); Jin Young Kim, Chungcheongbuk-do (KR); Ju Yeon Lee, Daejeon (KR)

(73) Assignee: KOREA BASIC SCIENCE INSTITUTE, Daejeon (KR)

( * ) Notice: Subject to any disclaimer, the term of this patent is extended or adjusted under 35 U.S.C. 154(b) by 0 days.

(21) Appl. No.: 15/545,552

(22) PCT Filed: Apr. 27, 2017

(86) PCT No.: PCT/KR2017/004484
§ 371 (c)(1),
(2) Date: Jul. 21, 2017

(87) PCT Pub. No.: WO2018/194203
PCT Pub. Date: Oct. 25, 2018

(65) Prior Publication Data
US 2020/0018759 A1    Jan. 16, 2020

(30) Foreign Application Priority Data
Apr. 20, 2017  (KR) .................. 10-2017-0051054

(51) Int. Cl.
*G01N 33/574* (2006.01)
*G01N 33/68* (2006.01)

(52) U.S. Cl.
CPC ... *G01N 33/57438* (2013.01); *G01N 33/6851* (2013.01); *G01N 2333/471* (2013.01); *G01N 2333/4728* (2013.01); *G01N 2440/38* (2013.01); *G01N 2560/00* (2013.01); *G01N 2800/085* (2013.01)

(58) Field of Classification Search
CPC ......... G01N 33/57438; G01N 33/6851; G01N 2560/00; G01N 2440/38; G01N 2800/085; G01N 2333/471; G01N 2333/4728; G01N 2240/38
See application file for complete search history.

(56) References Cited

U.S. PATENT DOCUMENTS

| 8,119,356 B2* | 2/2012 | Ko ................. G01N 33/54313 435/7.1 |
| 9,938,561 B2* | 4/2018 | Kim ........................ C12Q 1/34 |
| 2012/0190576 A1 | 7/2012 | Narimatsu et al. |
| 2016/0168618 A1* | 6/2016 | Kim ........................ C12Q 1/34 435/23 |

OTHER PUBLICATIONS

Li et al. "AFP-L3: a new generation of tumor marker for hepatocellular carcinoma" *Clinica Chimica Acta*, 313:15-19 (2001).
Anderson and Anderson "The Human Plasma Proteome" *Molecular & Cellular Proteomics*, 846-867 (2002).
Kim et al. "Measurement of Glycosylated Alpha-Fetoprotein Improves Diagnostic Power over the Native Form in Hepatocellular Carcinoma" *PLOS ONE*, 9(10):1-12 (2014).
Kim et al. "Quantitative analysis of low-abundance serological proteins with peptide affinity-based enrichment and pseudo-multiple reaction monitoring by hybrid quadrupole time-of-flight mass pectrometry" *Analytica Chimica Acta*, 882:38-48 (2015).
Pinho et al. "Glycosylation in cancer: mechanisms and clinical implications" Nature Reviews Cancer *Nature Reviews Cancer*, 15(9):540-555 (2015).
Kim et al. "Measurement of Glycosylated Alpha-Fetoprotein Improves Diagnostic Power over the Native Form in Hepatocellular Carcinoma" *PLOS One* vol. 9(10):1-12 e110366, 2004.

* cited by examiner

*Primary Examiner* — Marcela M Cordero Garcia
(74) *Attorney, Agent, or Firm* — Klarquist Sparkman, LLP (57) ABSTRACT

The present invention relates to a diagnosis method of liver cancer using mass spectrometry of α-fetoprotein derived glycopeptide. Particularly, according to the AFP glycopeptide analysis method of the invention, fucosylation rate of the glycopeptide having the sequence composed of Val-Asn-Phe-Thr-Glu-Ile-Gln-Lys is analyzed to diagnose liver cancer in the early developmental grade. In particular, fucosylation rate is higher in the liver cancer patients than in other liver disease patients, so that the comparison of the fucosylation rate can be useful to diagnose or distinguish liver cancer from other liver diseases in the early HCC patients.

13 Claims, 3 Drawing Sheets
Specification includes a Sequence Listing.

DIAGNOSTIC METHOD OF LIVER CANCER USING α-FETOPROTEIN DERIVED GLYCOPEPTIDES BY MASS SPECTROMETRY

TECHNICAL FIELD

The present invention relates to a diagnosis method of liver cancer using mass spectrometry of α-fetoprotein (AFP) derived glycopeptide.

BACKGROUND ART

Glycoprotein is a factor involved in various life activities of the human body. Thus, it is important to understand the functional changes of the glycoprotein. Proteins produced in cells are translated according to their functions and then modified, which is 'post-translational modification', by which they become different glycoproteins having diverse sugar chain structures and accordingly having different unique functions. Glycosylation is the most representative protein modification. Secretory proteins derived from cancer cells or surface proteins of cell membrane are non-specifically glycosylated by oncogene, thereby causing cancer. The relationship between cancer development and glycosylation has been studied extensively and the results confirmed that cancer could be developed by the cancer-specific glycosylation (Salome S. et al., Nature Reviews Cancer, 2015, 15(9):540-550).

The abnormal glycosylation in glycoprotein is fucosylation, sialylation, and polylactosamine, etc. Analysis of such abnormal glycosylation can be used to collect clinical information for cancer diagnosis and prognosis. Such glycoproteins that can give clinically useful information can be used as cancer biomarkers. Effective methods for the development and validation of cancer biomarkers have been developed. A glycoprotein capable of providing cancer-related information can be used to diagnose cancer by detecting the glycoprotein in a culture medium of cancer cells, a lysate of cancer tissue, or blood. At this time, blood which is easy to collect as a sample is mainly used. Therefore, it is important to analyze glycoprotein, the cancer biomarker, in a blood sample. However, the amount of glycoprotein in blood is very small for efficient analysis, so an effective method with high sensitivity and accuracy is required.

To diagnose cancer, a technique that can clearly distinguish cancer patients from normal people is important. In particular, various analytical methods have been developed to analyze protein glycosylation for cancer diagnosis. Among those methods, an analytical method for separating and concentrating a target sugar chain to be analyzed using a lectin protein that reacts with a specific sugar chain is most widely used. The blood used as an analytical sample has a rather complicated composition, so the method to separate and concentrate glycoproteins using a lectin protein seems more efficient for the analysis of a specific sugar chain structure. The separated and concentrated glycoprotein can be analyzed by spectroscopic methods to obtain the final results.

Lectin-blotting is an example of the glycoprotein analysis method using a lectin protein. This method is based on immunoblotting using a specific antibody selectively binding to the glycoprotein having a specific sugar chain structure. The lectin-blotting method can selectively separate and concentrate the marker glycoprotein having a specific sugar chain structure by using the selective binding capacity of lectin to the sugar chain structure of the glycoprotein. In the method above, various lectin proteins such as ConA (concanavalin A), WGA (wheat germ agglutinin), jacalin, SNA (sambucus nigra agglutinin), AAL (aleuria aurantia lectin), LPHA (phytohemagglutinin-L), PNA (peanut agglutinin), LCA (lens culimaris agglutinin-A), and DSA (datura stramonium agglutinin) can be used according to the structure of the sugar chain to be separated and concentrated (Yang Z. et al., J. Chromatography, 2001, 1053:79-88; Wang Y. et al., Glycobiology, 2006, 16:514-523). However, the lectin-blotting method is a gel-based analysis technique, so the analysis speed and the reliability of the result might be limited.

The unsatisfactory analysis speed and reliability can be improved by using lectin/enzyme-linked immunosorbent assay (lectin/ELISA) based on sandwich array (Forrester S. et al., Cancer Mol. Oncol., 2007, 1(2):216-225). Sandwich array uses the primary and the secondary antibodies for the analysis. At this time, non-specific reactions can be occurred due to the cross-reactivity of the secondary antibodies, which might results in poor reproducibility of results. This method is not so economical because of using two antibodies.

In the meantime, high-speed/high-sensitivity qualitative/quantitative analysis using a mass spectrometer is also used for the analysis of glycoprotein. In particular, multiple reaction monitoring mass spectrometry (MRM) facilitates quantification of the peptide produced from protein hydrolysis, which is highly reliable. This method allows relatively quick and accurate analysis results from the blood samples having complicated composition. According to MRM, a target peptide generated from the hydrolysis of a target glycoprotein is analyzed by liquid chromatography at least once and precursor mass selection and product ion selection at least twice, enabling selective analysis with high sensitivity using the sample as blood.

Recently, a parallel reaction monitoring (PRM) technique has been known (Peterson et al., Mol. Cell Proteomics, 2012, 11(11):1475-1488). Unlike MRM, this method uses a mass spectrometer equipped with a trap and time-of-flight mass analyzer, so that a product ion spectrum of the peptide can be obtained, allowing quantitative and qualitative analysis of the peptide simultaneously. This method can analyze trace glycoproteins that exhibit low signals with high reproducibility and excellent sensitivity (Kim et al., Analytica Chimica acta., 2015(882):38-48).

The methods for analyzing a specific sugar chain using a mass spectrometer include the method based on the analysis of the sugar chain separated from glycoproteins, the method based on the analysis of the sugar chain bound glycopeptide, and the method based on the analysis of the sugar chain bound glycoprotein. The sugar chains bound to the protein by modification have various structures and exhibit heterogeneity of the sugar chain having various structures at the same amino acid position and at the same time. It is also expected that the position of the amino acid to which the sugar chain can bind varies, and the role of the sugar chain varies depending on the position. Therefore, it is important to analyze the glycopeptide site-specifically.

Proteins are rich in serum that has been used as a sample for disease diagnosis. Among them, about 10 high concentration proteins take almost 90% of the total mass of blood. However, well known biomarker proteins have a relatively low concentration, which makes the accurate detection in a sample difficult (Anderson N. L. et al., Cell Proteomics, 2002, 1:845-867). Therefore, a pretreatment process that minimizes the complexity of the serum is required to analyze the biomarkers in the serum. To do so, such methods as depletion to eliminate the high concentration proteins and antibody-based immunoprecipitation to selectively concentrate a target protein can be used. In particular, when a selected biomarker is well known as in the case of cancer, it is efficient to use an immunoprecipitation method by selecting an effective antibody against the biomarker.

Hepatocellular carcinoma is about 76% of total liver cancer. The causes of hepatocellular carcinoma include chronic hepatitis B, chronic hepatitis C, cirrhosis, alcoholic liver disease, and diabetic liver disease. In particular, hepatitis B is a high risk factor, which is the cause of 72% of the total hepatocellular carcinoma in Korea. Hepatocellular carcinoma occurs in about one third of patients with liver cirrhosis. Therefore, it is highly desirable to develop a cancer biomarker capable of diagnosing progression from liver disease to hepatocellular carcinoma. Hepatocellular carcinoma does not show symptoms until it progresses significantly. So, a regular examination is needed, otherwise the treatment is very limited. In order for the treatment to be efficient, early diagnosis technique is required.

Therefore, in the course of study to identify a biomarker useful for the diagnosis of cancer, the present inventors confirmed that liver cancer patients and liver disease patients such as cirrhosis patients or hepatitis patients can be distinguished by calculating the rate of fucosylation of AFP glycopeptide, leading to the completion of the present invention.

DISCLOSURE

Technical Problem

It is an object of the present invention to provide a diagnosis method of liver cancer by calculating the rate of fucosylation of AFP glycopeptide separated from a sample.

Technical Solution

To achieve the object above, the present invention provides a method for analyzing AFP glycopeptide to provide the information useful for the liver cancer diagnosis which comprises the following steps: separating α-fetoprotein (AFP) from the sample obtained from a subject; obtaining AFP glycopeptide by hydrolyzing the separated AFP above; analyzing the mass and quantity of the obtained AFP glycopeptide; selecting the glycopeptide containing the sequence composed of Val-Asn-Phe-Thr-Glu-Ile-Gln-Lys (VNFTEIQK, SEQ ID NO: 1) and having the molecular weight of 2600.1±0.5, 2746.2±0.5, 2891.2±0.5, 3037.2±0.5, 3182.3±0.5, or 3328.3±0.5 Da; and calculating the rate of fucosylation of the selected glycopeptide and comparing the calculation result with that of the sample separated from a subject having liver cirrhosis or hepatitis.

Advantageous Effects

The analysis method of AFP glycoprotein of the present invention analyzes the rate of fucosylation of the glycopeptide containing the sequence comprising Val-Asn-Phe-Thr-Glu-Ile-Gln-Lys (SEQ ID NO: 1), so that it can diagnose liver cancer in its early developmental grade. Compared with other liver disease patients, liver cancer patients display higher fucosylation rate. Therefore, the method of the invention can be effectively used for diagnosing and distinguishing liver cancer from other liver diseases.

DESCRIPTION OF DRAWINGS

The application of the preferred embodiments of the present invention is best understood with reference to the accompanying drawings, wherein.

BEST MODE

Hereinafter, the present invention is described in detail.

The present invention provides a method for analyzing AFP glycopeptide to provide the information useful for the liver cancer diagnosis which comprises the following steps: separating α-fetoprotein (AFP) from the sample obtained from a subject; obtaining AFP glycopeptide by hydrolyzing the separated AFP above; analyzing the mass and quantity of the obtained AFP glycopeptide; selecting the glycopeptide containing the sequence composed of Val-Asn-Phe-Thr-Glu-Ile-Gln-Lys (VNFTEIQK, SEQ ID NO: 1) and having the molecular weight of 2600.1±0.5, 2746.2±0.5, 2891.2±0.5, 3037.2±0.5, 3182.3±0.5, or 3328.3±0.5 Da; and calculating the rate of fucosylation of the selected glycopeptide and comparing the calculation result with that of the sample separated from a subject having liver cirrhosis or hepatitis.

The method for analyzing AFP glycopeptide to provide the information useful for the liver cancer diagnosis of the present invention comprises a step of separating AFP from the sample obtained from a subject.

The sample herein might include a protein that contains information related to the presence or progress of liver cancer. Since the glycopeptide used in this analysis method of the invention is generally secreted from cells or tissues when the action is completed, the sample can include a cancer cell culture medium or blood of a patient. Particularly, the sample herein can be one or more materials selected from the group consisting of tissue, cell, cell culture fluid, blood, and serum, and more preferably blood or serum. In a preferred embodiment of the present invention, the sample is serum.

The AFP separation may be a pretreatment for reducing complexity of the serum sample in order to analyze AFP present in the serum in trace amounts. Particularly, AFP separation realizes the elimination of albumin, immunoglobulin G, and immunoglobulin A, taking at least 90% of the total serum. The separation can be performed by any method known to those in the art which is capable of selectively separating AFP. Separation of AFP can improve the detection limit and quantification limit of AFP present in the serum in trace amounts. In a preferred embodiment of the present invention, the separation was performed by immunoprecipitation.

As an example, the separation can be performed by using the anti-AFP antibody. The anti-AFP antibody herein can be a monoclonal antibody, a polyclonal antibody, or a mixture thereof, or an antibody fragment. The antibody fragment herein can be a functional fragment of an antibody molecule that contains the capacity of linking with a target antigen. Particularly, the antibody fragment herein can contain Fab, F(ab'), F(ab')2, and Fv. The antibody can be easily constructed by the conventional technique well known to those in the art.

The anti-AFP antibody above can be linked to magnetic beads. The magnetic bead surface may be tosylated or epoxidated, specifically tosylated. The magnetic bead herein is preferably combined with streptavidin, protein G, or protein A.

The method for analyzing AFP glycopeptide to provide the information useful for the liver cancer diagnosis of the present invention comprises a step of obtaining AFP glycopeptide by hydrolyzing the separated AFP.

In this step, smaller glycopeptide fragments can be obtained by hydrolysis to improve the mass spectrometry efficiency of AFP having a higher molecular weight. The enzyme which can be used for the hydrolysis is one or more enzymes selected from the group consisting of arginine C (arg-C), aspartic acid N (asp-N), glutamic acid C (glu-C), chymotrypsin, and trypsin. In a preferred embodiment of the present invention, the enzyme used for the hydrolysis was trypsin.

In the method of the invention, the hydrolysis is performed after such pretreatments as denaturation, reduction, and cysteine alkylation by those in the art in order to improve the analysis efficiency of a target glycopeptide.

The method for analyzing AFP glycopeptide to provide the information useful for the liver cancer diagnosis of the present invention comprises a step of analyzing the mass and quantity of the obtained AFP glycopeptide.

The mass of AFP glycopeptide can be determined by analyzing the glycopeptide including glycosylation sites due to glycan microheterogeneity sharing the structures of various sugar chains in the same glycosylation site. The mass can be analyzed by using a mass spectrometer.

The mass analysis can be performed by parallel reaction monitoring mass spectrometry (PRM), multiple reaction monitoring mass spectrometry (MRM), or single reaction monitoring mass spectrometry (SRM). Precisely, the mass analysis can be performed by PRM. In the meantime, the quantitative analysis can be performed by liquid chromatography-mass spectrometry (LC-MS), matrix-assisted laser desorption/ionization-mass spectrometry (MALDI-MS), or mass spectrometry using direct atomization.

The said PRM is one of the quantitative analysis methods using a mass spectrometer, which can give highly reliable results based on the ion selectivity of high resolution and product ion results. This method facilitates fast and sensitive analysis of a target material from such samples that have a complicated composition like blood.

MRM is a method of selectively analyzing only target ions by arranging three consecutive quadruple mass analyzers with low resolution. This method facilitates the accurate analysis of trace materials.

To increase the sensitivity and accuracy of the analysis, glycopeptide can be additionally concentrated before analyzing the mass and quantity of the AFP glycopeptide. The concentration can be performed by a proper method selected by those in the art.

The obtained glycopeptide can be additionally treated with a desialylation enzyme before analyzing the mass and quantity. The desialylation enzyme herein can be α2-3 neuraminidase or α2-3,6,8 neuraminidase. The method for analyzing AFP glycopeptide to provide the information useful for the liver cancer diagnosis of the present invention comprises a step of selecting the glycopeptide containing the sequence composed of Val-Asn-Phe-Thr-Glu-Ile-Gln-Lys (VNFTEIQK, SEQ ID NO: 1) and having the molecular weight of 2600.1±0.5, 2746.2±0.5, 2891.2±0.5, 3037.2±0.5, 3182.3±0.5, or 3328.3±0.5 Da. When the molecular weight of the glycopeptide is within 2891.2±0.5, 3037.2±0.5, 3182.3±0.5, or 3328.3±0.5 Da, the quantitative results for the three product ions ionized from one precursor ion can be showed as follows:

964.7→1181.6, 1118.5, and 1037.5
1013.4→1181.6, 1191.5, and 1110.5
1061.8→1181.6, 1118.5, and 1264.0
1110.5→1181.6, 1191.5, and 1337.1.

When the molecular weight of the glycopeptide is within 2600.1±0.5 or 2746.2±0.5 Da, the quantitative results for the three product ions ionized from one precursor ion can be showed as follows:

867.7→1181.6, 1118.5, and 1037.5
916.4→1181.6, 1191.5, and 1110.5.

The method for analyzing AFP glycopeptide to provide the information useful for the liver cancer diagnosis of the present invention comprises a step of calculating the rate of fucosylation of the selected glycopeptide and comparing the calculation result with that of the sample separated from a subject having liver cirrhosis or hepatitis.

The fucosylation rate, as described hereinbefore, can be obtained by parallel reaction monitoring mass spectrometry (PRM), multiple reaction monitoring mass spectrometry (MRM), or single reaction monitoring mass spectrometry (SRM), and more preferably can be obtained by PRM.

The comparison above is achieved by comparing the rate of fucosylation of AFP glycopeptide with that of a subject having liver cirrhosis or hepatitis. Precisely, if the fucosylation rate of AFP glycopeptide is increased significantly, it would be diagnosed as liver cancer. So, the method of the invention can be useful to distinguish a liver cancer patient from other liver disease patients.

In a preferred embodiment of the present invention, blood samples were obtained from liver cancer patients and liver disease patients and the AFP glycoprotein was separated from the obtained blood samples using a complex of magnetic beads and anti-AFP antibody. AFP glycopeptide was isolated from the AFP glycoprotein, and the mass and quantity of the separated AFP glycopeptide was analyzed. Then, the fucosylation ratio was calculated. As a result, the AFP glycopeptide composed of the sequence VNFTEIQK (SEQ ID NO: 1) was obtained. It was confirmed that the rate of fucosylation of AFP glycopeptide was increased significantly in liver cancer patients, compared with that in other liver disease patients (see FIG. 1). In particular, the fucosylation rate was significantly increased even in grade 1 liver cancer patients. Therefore, the method of the present invention was confirmed to be useful for diagnosing a liver cancer patient in the early grade from other liver disease patients (see FIG. 2).

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Blood Sample

Blood samples were obtained from 38 liver cancer patients and 21 other liver disease patients (control), from which sera were separated as experimental samples. Particularly, liver patients were divided according to the Edmondson-steiner level that determines the degree of liver cell cancer differentiation into grade 1, grade 2, and grade 3. Blood samples were obtained from 15 grade 1 patients, 15 grade 2 patients, and 8 grade 3 patients. In the meantime, control samples were obtained from 8 hepatitis patients and 13 liver cirrhosis patients.

Example 2: Separation of AFP Glycoprotein

AFP glycoprotein was separated from the serum by immunoprecipitation.
<2-1> Preparation of Magnetic Bead and Anti-AFP Antibody Conjugate
First, the magnetic bead and anti-AFP antibody conjugate was prepared for immunoprecipitation. Particularly, 5 mg of tosylactivated magnetic beads (Thermo Fisher Scientific, USA) was added to 500 μl of 0.1 M sodium borate for bead washing. The mixture was shaken by using an e-tube rotator. Then, the magnetic bead mixture was separated into sodium borate solution and magnetic beads by using an e-tube magnet, and sodium borate was eliminated thereafter. The above procedure was repeated to wash the beads four times, and 250 μg of anti-AFP antibody (Ab frontier, Korea), an AFP-specific universal monoclonal antibody prepared for immunoprecipitation, was added thereto. The mixture was reacted at 37° C. for 16 hours. At this time, 50 μl of ammonium sulfate was added to the reaction mixture above and pH of the reaction mixture was maintained at 9.5 to make the condition for the anti-AFP antibody to react with the magnetic beads. Upon completion of the reaction, the magnetic bead/anti-AFP antibody conjugate was washed with PBS (pH 7.4) containing 0.1% (w/v) BSA and 0.05% (v/v) tween 20. For the washing, washing buffer and the magnetic beads were separated from each other by using an e-tube magnet and then the solution was discarded, which was repeated three times. The washed conjugate was stored in storage buffer (pH 7.4) containing 0.1% (w/v) BSA, 0.05% (v/v) tween 20, and 0.02% (w/v) sodium azide at 4° C. until use.
<2-2> Separation of AFP Glycoprotein from Serum
AFP glycoprotein was separated from serum by using the magnetic bead/anti-AFP antibody conjugate constructed in Example <2-1> as follows.
Particularly, the magnetic bead/anti-AFP antibody conjugate containing 10 μg of antibody was taken, followed by washing with 50 mM ammonium bicarbonate and PBS three times with each. For the washing, washing buffer and the magnetic beads were separated from each other by using an e-tube magnet and then the solution was discarded, which was repeated three times. The washed magnetic bead/anti-AFP antibody conjugate was added with 24 μl of the serum, followed by reaction at room temperature for 2 hours. Upon completion of the reaction, the magnetic bead/anti-AFP antibody conjugate was washed with PBS three times. 40 μl of 0.1 M glycine buffer (pH 2) was added thereto in order to separate the antibody-conjugated AFP glycoprotein. More precisely, the separation was performed by the following steps: the magnetic beads were mixed with 40 μl of 0.1 M glycine buffer by using an e-tube rotator, and then the magnetic beads and 40 μl of 0.1 M glycine buffer were separated from each other by using an e-tube magnet to take out the solution alone. The separated AFP glycoprotein was dried under reduced pressure, and then suspended in 100 μl of 50 mM ammonium bicarbonate. The suspension was heated at 95° C. to denature the protein. Then, 5 mM dithiothreitol was added thereto, followed by reaction at 60° C. for 1 hour for the additional denaturation. 20 mM iodoacetic acid was added to the reaction mixture above, followed by alkylation for 1 hour. 10 μg of trypsin was added thereto, followed by hydrolysis at 37° C. The hydrolyzed AFP glycoprotein was treated with C18 cartridge for desalination. The obtained final sample was stored at −20° C. until it would be used for mass spectrometry.

Example 3: Confirmation of Glycopeptide Originated from AFP Glycoprotein

<3-1> Liquid Chromatography (LC)/MRM
In order to analyze the mass of the glycopeptide derived from AFP glycoprotein using the sample obtained in Example 2, LC/MRM was performed as follows.
Particularly, C18 (5 μm, 300 mm×5 mm) was used as the trap column and C18(5 μm, 75 μm×5 mm) was also used as the analysis column. The column was connected to TripleTOF mass spectrometer (SCIEX), the mass spectrometer operating based on the principle of electrospray ionization (ESI), followed by LC/MRM. The analysis was performed by injecting 4 μl of sample at the flow rate of 400 nl/min. At this time, an aqueous solution containing 0.1% (v/v) formic acid was used as the moving phase A and an acetonitrile solution containing 0.1% (v/v) formic acid was used as the moving phase B. The analysis was performed under the moving phase concentration gradient conditions shown in Table 1 below for 60 minutes.

TABLE 1

| Time (min) | Moving phase A (%) | Moving phase B (%) |
| --- | --- | --- |
| 0-1 | 95 | 5 |
| 1-35 | 95 →60 | 5 →40 |
| 35-37 | 60 →10 | 40 → 90 |
| 37-50 | 10 | 90 |
| 50-60 | 95 | 5 |

The results of LC/MRM were analyzed by using PeakView software. As a result, 6 kinds of AFP glycopeptides were selected as the liver cancer biomarkers, which are shown in Table 2.

TABLE 2

| AFP glycopeptide | MW | Precursor ion (m/z) | Product ion (m/z) |
| --- | --- | --- | --- |
| VNFTEIQK_5_4_0_0 SEQ ID NO: 2 | 2600.1 | 867.7 | 1181.6, 1037.5, 1118.5 |
| VNFTEIQK_5_4_1_0 SEQ ID NO: 3 | 2746.2 | 916.4 | 1181.6, 1110.5, 1191.5 |

TABLE 2-continued

| AFP glycopeptide | MW | Precursor ion (m/z) | Product ion (m/z) |
|---|---|---|---|
| VNFTEIQK_5_4_0_1 SEQ ID NO: 4 | 2891.2 | 964.7 | 1181.6, 1037.5, 1118.5 |
| VNFTEIQK_5_4_1_1 SEQ ID NO: 5 | 3037.2 | 1013.4 | 1181.6, 1110.5, 1191.5 |
| VNFTEIQK_5_4_0_2 SEQ ID NO: 6 | 3182.3 | 1061.8 | 1181.6, 1118.5, 1264.0 |
| VNFTEIQK_5_4_1_2 SEQ ID NO: 7 | 3328.3 | 1110.5 | 1181.6, 1191.5, 1337.1 |

As shown in Table 2, the AFP glycoprotein derived glycopeptides composed of the amino acid sequence of VNFTEIQK (SEQ ID NO: 1) were selected. The selected glycopeptides could be linked to 4 kinds of major monosaccharides forming N-sugar chain structure, Hexose_HexNAc (N-acetylhexoseamine)_Fucose_NeuAc(N-glycolylneuraminic acid) in that order, and the number of each monosaccharide is shown in the table. As a result, all the selected glycopeptides contained 5 Hexoses and 4 HexNAcs. According to the number of combined Fucose and NeuAc, they were presented as VNFTEIQK_5_4_0_1 (SEQ ID NO: 4), VNFTEIQK_5_4_1_1 (SEQ ID NO: 5), VNFTEIQK_5_4_0_2 (SEQ ID NO: 6), and VNFTEIQK_5_4_1_2 (SEQ ID NO: 7). NeuAc of the sugar chain was eliminated from the glycopeptide by using the desialylation enzymes α2-3 neuraminidase and α2-3,6,8 neurominidase, resulting in the two types of sugar chain conjugated glycopeptides VNFTEIQK_5_4_0_0 (SEQ ID NO: 2) and VNFTEIQK_5_4_1_0 (SEQ ID NO: 3), which were additionally selected.

Example 4: Confirmation of Fucosylation Rate of the Selected AFP Glycopeptide

The 6 kinds of glycopeptides selected in Example 3 are known as liver cancer and liver disease specific AFP derived glycopeptides. The percentage of fucosylation (Fuc %) was calculated by comparing the three non-fucosylated glycopeptides and the three fucosylated glycopeptides.

Particularly, LC/MRM mass analysis was performed three times by the same manner as described in Example 3. Based on the chromatography results obtained therefrom, peak area was calculated. The fucosylation rate (Fuc %) was calculated from the obtained peak area according to the math FIG. 1 below. At this time, 5_4_1_1 and 5_4_1_2 were used as the fucosylated glycopeptides and 5_4_0_1 and 5_4_0_2 were used as the non-fucosylated glycopeptides. In the meantime, in the case of the glycopeptides additionally selected by desialylation enzymes, 5_4_1_0 was used as the fucosylated glycopeptide and 5_4_0_0 was used as the non-fucosylated glycopeptide.

As a result, it was observed in the selected glycopeptides that 4 different sugar chains were linked to asparagine (N) site of the glycopeptide having the amino acid sequence of VNFTEIQK (SEQ ID NO: 1). Precursor ions having 3+ charge with showing the highest sensitivity in the mass spectrometer using each glycopeptide, m/z 867.7, 916.4, 964.7, 1013.4, 1061.8, and 1110.5, were proceeded to LC/MRM. Based on the results of MS/MS, three kinds of product ions, as shown in Table 2, were selected for LC/MRM. These product ions were compared with those corresponding ions in mass spectrometry results and sensitivity.

The selected product ions were produced from the AFP glycopeptide having a sugar chain. Among them, Y1 (1181.6) was included in every AFP glycopeptide. The Y1 product ion is a highly specific glycopeptide to the precursor ion to be analyzed in the form of only one HexNAc in the asparagine (N) site of VNFTEIQK (SEQ ID NO: 1). For the other two types, the product ions specific to the structure of each sugar chain were selected. Particularly, Y6 (1037.5) and Y7 (1118.5) were selected from the glycopeptide VNFTEIQK_5_4_0_1 (SEQ ID NO: 4). Y7 (1110.5) and Y8 (1191.5) were selected from VNFTEIQK_5_4_1_1 (SEQ ID NO: 5). Y7 (1118.5) and Y8 (1264.0) were selected from VNFTEIQK_5_4_0_2 (SEQ ID NO: 6). Y8 (1191.5) and Y9 (1337.1) were selected from VNFTEIQK_5_4_1_2 (SEQ ID NO: 7). In the meantime, Y6 (1037.5) and Y7 (1118.5) were selected from VNFTEIQK_5_4_0_0 (SEQ ID NO: 2), and Y7 (1110.5) and Y8 (1191.5) were selected from VNFTEIQK_5_4_1_0 (SEQ ID NO: 3).

Peak area was calculated based on the results of LC/MRM of three product ions specifically obtained from one glycopeptide. Combining all the results together, one chromatography result corresponding to each precursor ion was obtained. At this time, three product ions obtained from one precursor ion were used to improve the analysis sensitivity. The obtained final peak area value was put in the math FIG. 1 to calculate the fucosylation rate. The mean value was obtained from three repeats. From the results, scatter plot of each liver cancer and liver disease (hepatitis or liver cirrhosis) was made and shown in FIG. 1 and FIG. 2. ROC curve is shown in FIG. 3.

Figure 1:
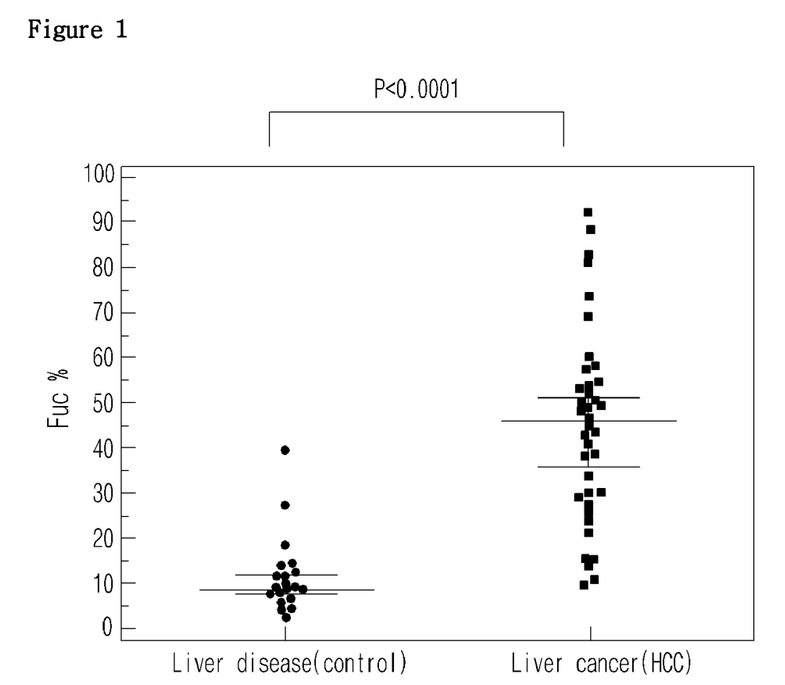
FIG. 1 is a graph illustrating the comparison of the rate of fucosylation of AFP glycopeptides separated from liver cancer patients and liver disease patients.

[Math FIG. 1]

$$\text{Fucosylation rate}(\%) = \frac{\text{Fucosylated glycopeptide}}{(\text{Non-fucosylated glycopeptide} + \text{fucosylated glycopeptide})} \times 100$$

Figure 2:
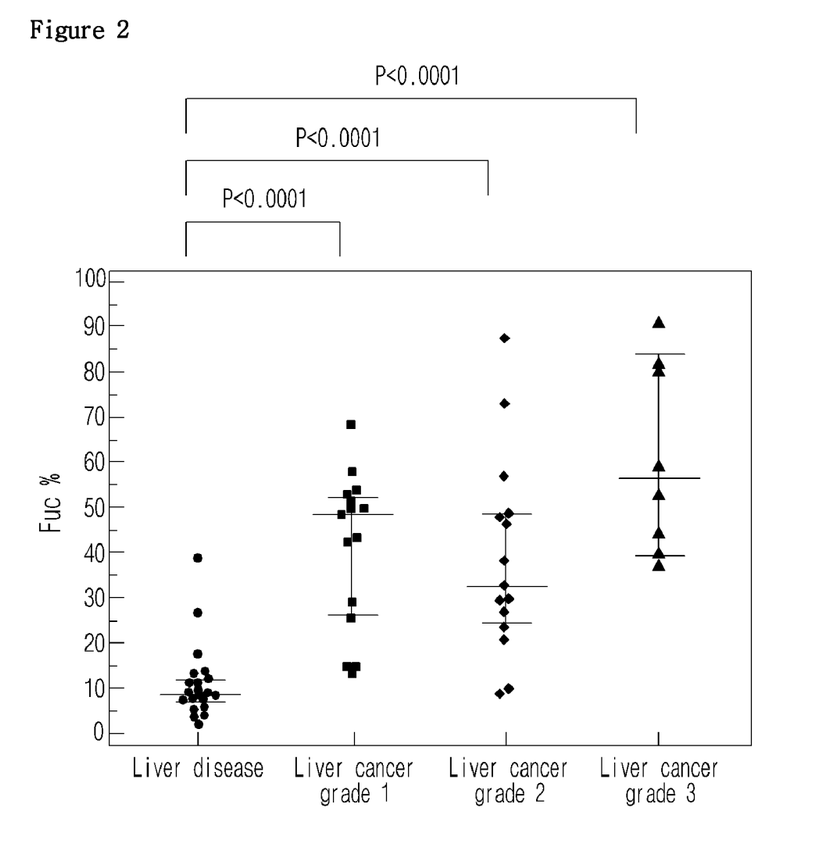
FIG. 2 is a graph illustrating the comparison of the rate of fucosylation of AFP glycoproteins separated from liver cancer patients (grade 1, grade 2, and grade 3) and liver disease patients.
Figure 3:
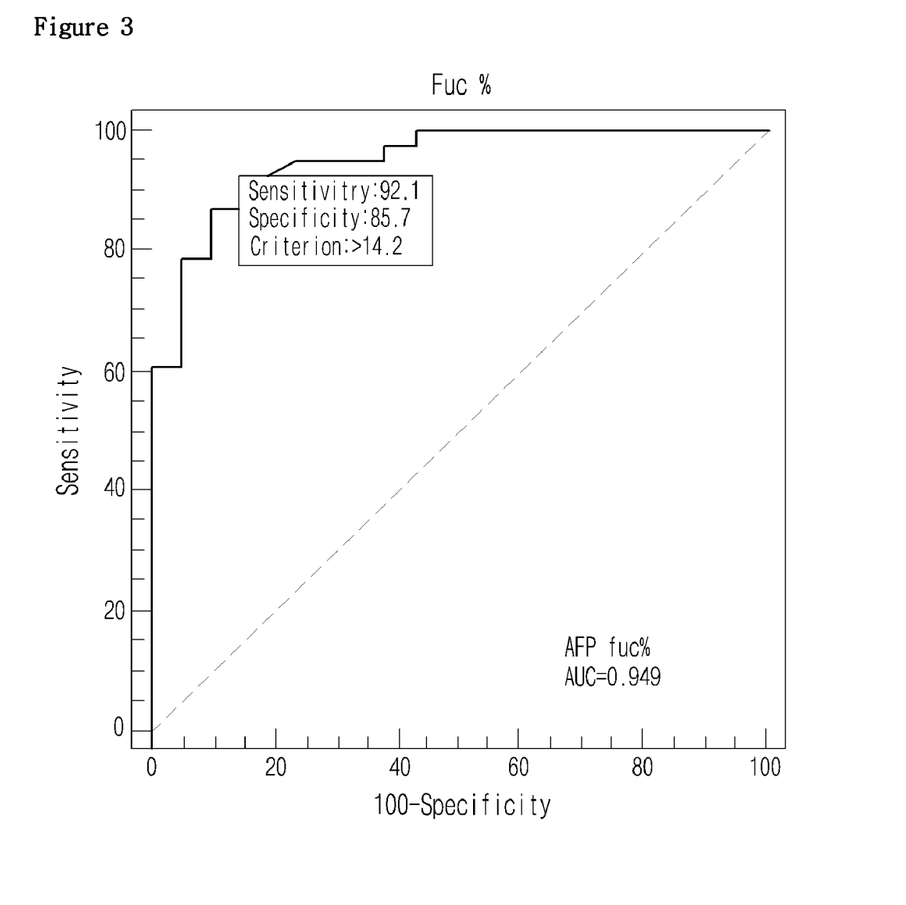
FIG. 3 is a graph illustrating the ROC (receiver operating characteristic) curve and AUC (area under the ROC curve) based on the comparison of the rate of fucosylation of AFP glycopeptides separated from liver cancer patients and liver disease patients.

As shown in FIGS. 1 and 2, the fucosylation rate of AFP glycopeptide in the serum separated from the liver cancer patient group was significantly increased, compared with that of the liver disease patient group (FIG. 1). Particularly, the mean value of the liver disease group was 8.8% and the fucosylation rate in at least 90% of liver disease patients was up to 20%. In the meantime, the mean value of the liver cancer patient group was 46.0% and the fucosylation rate in approximately 87% of liver cancer patients was at least 20%. As shown in FIG. 2, the fucosylation rate of the grade 1 liver cancer group and grade 3 liver cancer group was respectively increased about 6 times higher than that of the liver disease group and about 4 times higher in the grade 2 liver cancer group (FIG. 2).

ROC curve was made based on the results of FIG. 1. As a result, AUROC (area under ROC) was 0.949, suggesting that the method above has 85.7% of marker specificity and 92.1% of sensitivity.

Therefore, it was confirmed that the method of the invention was efficient to distinguish liver cancer patients from other liver disease patients. Particularly, the method was confirmed to be very useful to diagnose early grade liver cancer because the AFP glycopeptide fucosylation rate was significantly high in grade 1 liver cancer patients, compared with other liver disease patients.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

The invention claimed is:

1. A method for analyzing AFP glycopeptide which comprises the following steps:
   1) separating α-fetoprotein (AFP) from a sample obtained from a subject, wherein the subject is a liver cancer patient or other liver disease patient;
   2) obtaining AFP glycopeptide by hydrolyzing the AFP separated in step 1);
   3) analyzing the mass and quantity of the AFP glycopeptide obtained in step 2) by parallel reaction monitoring mass spectrometry (PRM), multiple reaction monitoring mass spectrometry (MRM), or single reaction monitoring mass spectrometry (SRM);
   4) selecting the glycopeptide containing the sequence composed of Val-Asn-Phe-Thr-Glu-Ile-Gln-Lys_(VNFTEIQK, SEQ ID NO: 1) and having the molecular weight of 2600.1±0.5, 2746.2±0.5, 2891.2±0.5, 3037.2±0.5, 3182.3±0.5, or 3328.3±0.5 Da; and
   5) calculating the rate of fucosylation of the glycopeptide selected in step 4) by PRM, MRM, or SRM and comparing the calculation result with that of a sample separated from a subject having liver cirrhosis or hepatitis.

2. The method for analyzing AFP glycopeptide according to claim 1, wherein the sample is one or more materials selected from the group consisting of tissue, cell, cell culture fluid, blood, and serum.

3. The method for analyzing AFP glycopeptide according to claim 1, wherein the separation of step 1) is performed by using an anti-AFP antibody.

4. The method for analyzing AFP glycopeptide according to claim 3, wherein the anti-AFP antibody is a monoclonal antibody, a polyclonal antibody, or a mixture thereof.

5. The method for analyzing AFP glycopeptide according to claim 3, wherein the anti-AFP antibody is conjugated to magnetic beads.

6. The method for analyzing AFP glycopeptide according to claim 5, wherein the magnetic bead surface is tosylated or epoxidated.

7. The method for analyzing AFP glycopeptide according to claim 5, wherein the magnetic bead is conjugated to streptavidin, protein G, or protein A.

8. The method for analyzing AFP glycopeptide according to claim 1, wherein the hydrolysis of step 2) is performed using one or more enzymes selected from the group consisting of arg-C, asp-N, glu-C, chymotrypsin, and trypsin.

9. The method for analyzing AFP glycopeptide according to claim 1, wherein the analysis of step 3) is performed by liquid chromatography-mass spectrometry (LC-MS), matrix-assisted laser desorption ionization (MALDI-MS), or direct infusion.

10. The method for analyzing AFP glycopeptide according to claim 1, wherein a step of concentrating the glycopeptide obtained in step 2) is additionally included before step 3).

11. The method for analyzing AFP glycopeptide according to claim 1, wherein if the molecular weight of the glycopeptide analyzed in step 3) is within 2891.2±0.5, 3037.2±0.5, 3182.3±0.5, or 3328.3±0.5 Da, then the quantitative results for the three product ions ionized from one precursor ion can be shown as follows:

964.7→1181.6, 1118.5, and 1037.5
1013.4→1181.6, 1191.5, and 1110.5
1061.8→1181.6, 1118.5, and 1264.0; and
1110.5→1181.6, 1191.5, and 1337.1, respectively.

12. The method for according to claim 1, wherein the step of treating a desialylation enzyme to the glycopeptide obtained in step 2) is additionally included.

13. The method for analyzing AFP glycopeptide according to claim 12, wherein if the molecular weight of the glycopeptide analyzed in step 3) is within 2600.1±0.5 or 2746.2±0.5 Da, then the quantitative results for the three product ions ionized from one precursor ion can be shown as follows:

867.7→1181.6, 1118.5 and 1037.5; and
916.4→1181.6, 1191.5 and 1110.5, respectively.

* * * * *

SEQUENCE LISTING

```
<160> NUMBER OF SEQ ID NOS: 7

<210> SEQ ID NO 1
<211> LENGTH: 8
<212> TYPE: PRT
<213> ORGANISM: Homo sapiens

<400> SEQUENCE: 1

Val Asn Phe Thr Glu Ile Gln Lys
1               5

<210> SEQ ID NO 2
<211> LENGTH: 8
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: 5 Hexose and 4 HexNAc (N-acetylhexoseamine) (in
      order)

<400> SEQUENCE: 2

Val Asn Phe Thr Glu Ile Gln Lys
1               5

<210> SEQ ID NO 3
<211> LENGTH: 8
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: 5 Hexose, 4 HexNAc (N-acetylhexoseamine), and 1
      Fucose (in order)

<400> SEQUENCE: 3

Val Asn Phe Thr Glu Ile Gln Lys
1               5

<210> SEQ ID NO 4
<211> LENGTH: 8
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: 5 Hexose, 4 HexNAc (N-acetylhexoseamine), and 1
      NeuAc (N-glycolylneuraminic acid)(in order)

<400> SEQUENCE: 4

Val Asn Phe Thr Glu Ile Gln Lys
```

```
<210> SEQ ID NO 5
<211> LENGTH: 8
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: 5 Hexose, 4 HexNAc (N-acetylhexoseamine), 1
      Fucose, and 1 NeuAc (N-glycolylneuraminic acid) (in order)

<400> SEQUENCE: 5

Val Asn Phe Thr Glu Ile Gln Lys
1               5

<210> SEQ ID NO 6
<211> LENGTH: 8
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: 5 Hexose, 4 HexNAc (N-acetylhexoseamine), and 2
      NeuAc (N-glycolylneuraminic acid) (in order)

<400> SEQUENCE: 6

Val Asn Phe Thr Glu Ile Gln Lys
1               5

<210> SEQ ID NO 7
<211> LENGTH: 8
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: 5 Hexose, 4 HexNAc (N-acetylhexoseamine), 1
      Fucose, and 2 NeuAc (N-glycolylneuraminic acid) (in order)

<400> SEQUENCE: 7

Val Asn Phe Thr Glu Ile Gln Lys
1               5
```